(12) United States Patent
Berndt

(10) Patent No.: US 9,709,516 B2
(45) Date of Patent: Jul. 18, 2017

(54) IMPEDANCE-BASED BACTERIAL DETECTION SYSTEM

(71) Applicant: Becton, Dickinson and Company, Franklin Lakes, NJ (US)

(72) Inventor: Klaus W. Berndt, Cockeysville, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/378,547

(22) PCT Filed: Feb. 14, 2013

(86) PCT No.: PCT/US2013/026138
§ 371 (c)(1),
(2) Date: Aug. 13, 2014

(87) PCT Pub. No.: WO2013/123189
PCT Pub. Date: Aug. 22, 2013

(65) Prior Publication Data
US 2015/0005196 A1 Jan. 1, 2015

Related U.S. Application Data

(60) Provisional application No. 61/599,100, filed on Feb. 15, 2012.

(51) Int. Cl.
G01N 27/02 (2006.01)
C12Q 1/04 (2006.01)
C12M 1/34 (2006.01)
G01N 33/487 (2006.01)

(52) U.S. Cl.
CPC ............ *G01N 27/02* (2013.01); *C12M 41/36* (2013.01); *C12Q 1/04* (2013.01); *G01N 27/026* (2013.01); *G01N 33/48735* (2013.01)

(58) Field of Classification Search
CPC ................. G01N 27/02; G01N 27/026; G01N 33/48735; C12M 41/36
See application file for complete search history.

(56) References Cited

U.S. PATENT DOCUMENTS

| 5,716,798 A | 2/1998 | Monthony et al. |
| 5,770,440 A | 6/1998 | Berndt |
| 5,891,739 A | 4/1999 | Berndt |
| 6,096,272 A | 8/2000 | Clark et al. |
| 6,764,583 B2 * | 7/2004 | Miles ............... G01N 33/48714 204/400 |
| 2002/0197709 A1 * | 12/2002 | Van der Weide ...... C12M 23/12 435/288.4 |
| 2007/0090927 A1 | 4/2007 | Potyrailo et al. |
| 2011/0081676 A1 | 4/2011 | Sengupta et al. |
| 2011/0086352 A1 | 4/2011 | Bashir et al. |

FOREIGN PATENT DOCUMENTS

| EP | 2243824 A1 | 10/2010 |
| JP | SHO 50-3695 | 1/1975 |
| JP | SHO 53-52681 | 5/1978 |
| JP | 2002-330752 | 11/2002 |
| JP | 2005-241404 | 9/2005 |
| JP | 2006-145216 | 6/2006 |
| JP | 2007-071766 | 3/2007 |
| JP | 2009-244197 | 10/2009 |
| WO | 2004010103 A2 | 1/2004 |
| WO | 2009136157 A2 | 11/2009 |

OTHER PUBLICATIONS

Bernabini et al. "Micro-impedance cytometry for detection and analysis of micron-sized particles and bacteria." (2010) Lab on a Chip, vol. 11: 407-412.*
International Search Report and Written Opinion for Application No. PCT/US2013/026138 dated May 27, 2013.
Puttaswamy, S., et al., "Novel Electrical Method for Early Detection of Viable Bacteria in Blood Cultures," J. Clin. MicroBio., vol. 49 (6), pp. 2286-2289 (2011).
Sengupta, S, et al., "A micro-scale multifrequency reactance measurement technique to detect bacterial growth at low bio-particle concentrations," Lab Chip, vol. 6, pp. 682-692 (2006).
Sengupta, S., et al., "Rapid detection of bacterial proliferation in food samples using microchannel impedance measurements at multiple frequencies," Scns. & Instrumen. Food Qual., vol. 4, pp. 108-118 (2010).
Supplementary European Search Report for Application No. EP13749418 dated Oct. 7, 2015.
Japanese Office Action for Application No. 2014-557770 dated Mar. 7, 2017.

\* cited by examiner

*Primary Examiner* — Teresa E Knight
(74) *Attorney, Agent, or Firm* — Lerner, David, Littenberg, Krumholz & Mentlik, LLP

(57) ABSTRACT

A method and apparatus for determining the presence or absence of microorganisms in a liquid sample. A vessel with an electrode disposed therein receives a volume of liquid to be tested. A second electrode is also provided, both electrodes in physical contact with the liquid sample. A time varying signal is applied to one electrode, and the other electrode is coupled to a phase sensitive signal detector. The phase sensitive signal detector determines a frequency at which an out of phase signal amplitude is zero. This zero-crossing frequency is used as a baseline, and changes in the zero-crossing frequency are an indication of microbial growth.

14 Claims, 14 Drawing Sheets

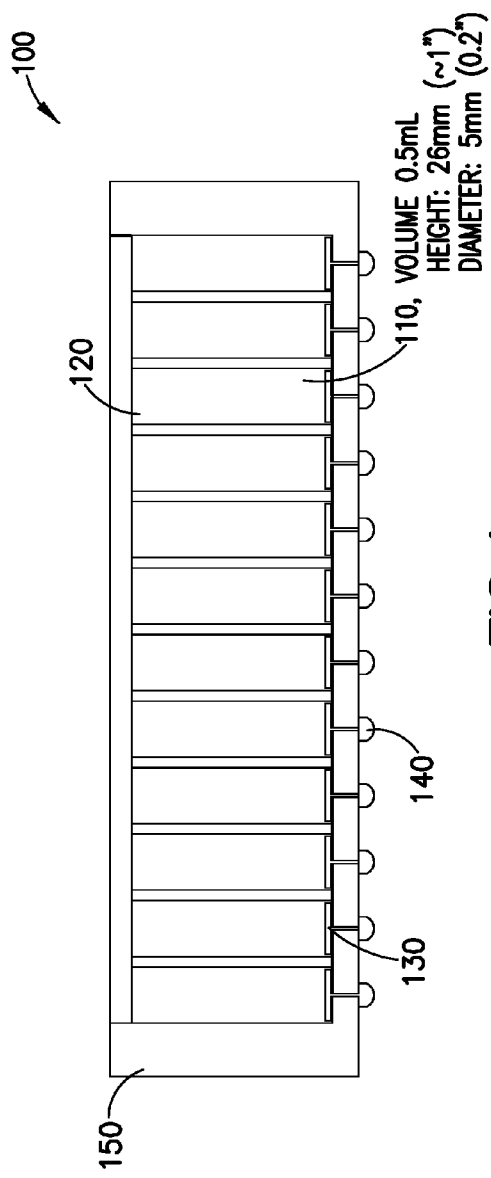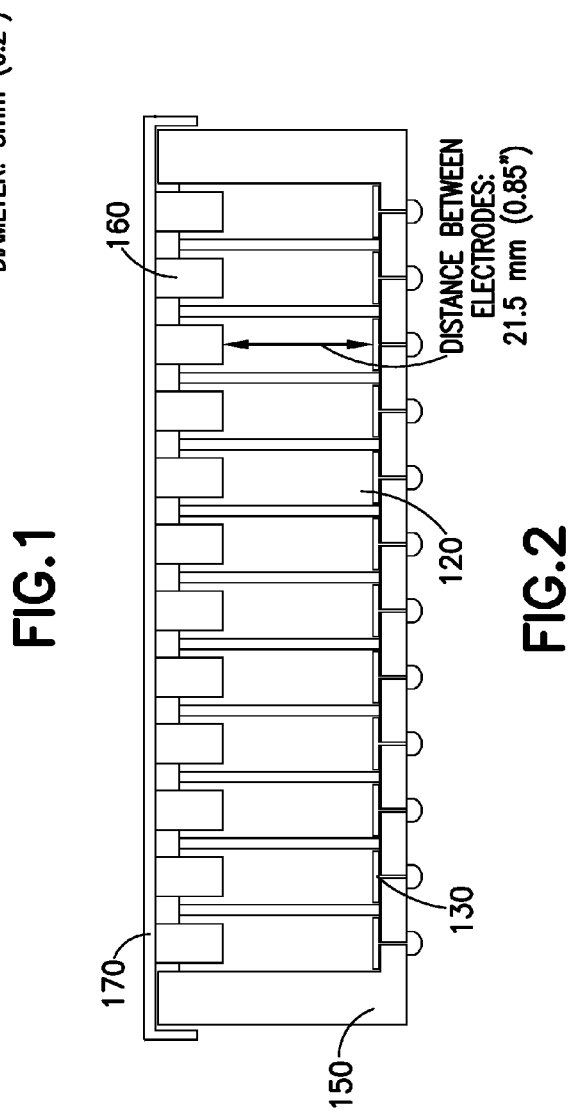

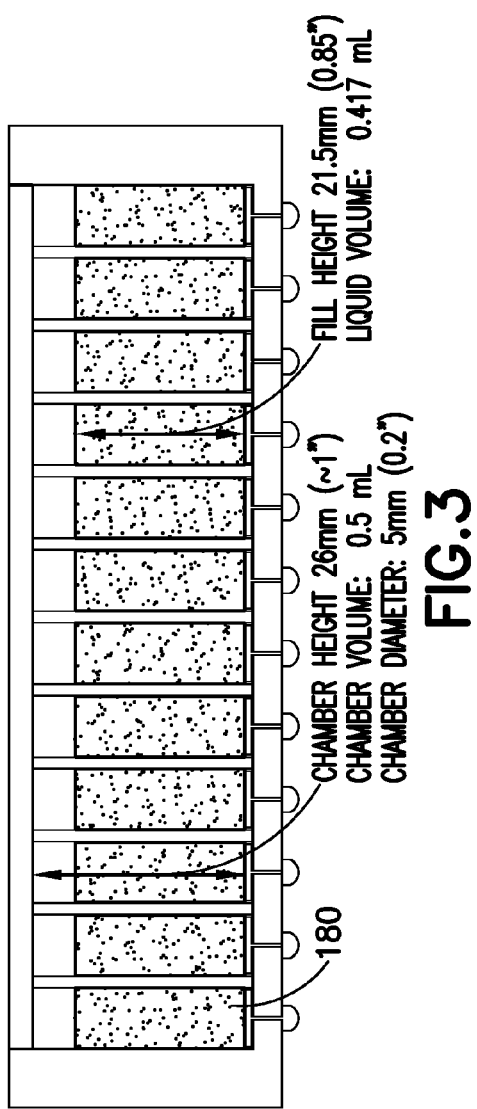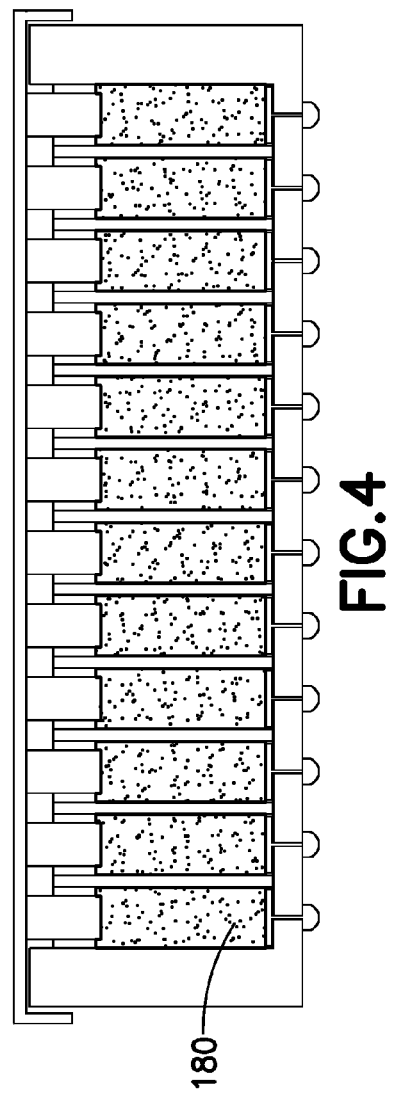

IMPEDANCE-BASED BACTERIAL
DETECTION SYSTEM

CROSS-REFERENCE TO RELATED APPLICATIONS

The present application is a national phase entry under 35 U.S.C. §371 of International Application No. PCT/US2013/026138, filed Feb. 14, 2013, published in English, which claims priority from U.S. Patent Application No. 61/599,100, filed Feb. 15, 2012, all of which are hereby incorporated herein by reference.

BACKGROUND OF THE INVENTION

The present invention relates to the field of microbial detection in clinical samples. The invention is in particular related to achieving faster detection of the presence or absence of bacteria in a biological sample.

The detection of the presence or absence of microbes (e.g. bacteria) in a biological sample is a necessary aspect of health care. Typically such detection requires that the microbes be cultured to provide enough microbes to be detected. There is a broad array of culture media for the growth of microbes in a sample, as the presence or absence of the microbes in the sample can only be determined if the quantity of microbes in the test sample is sufficient to ensure that the microbes will be detected if they are present.

For example, bacteria in clinical blood samples are typically detected by inoculating approximately 10 ml of whole blood in a culture bottle containing approximately 30 mL of growth media to support bacterial multiplication. The sample incubates in the bottle in an automated system at 35° C. The sample is monitored for the byproducts of cell metabolism or cell growth to determine the presence or absence of bacteria in the sample. In one example, the products of bacterial metabolism (such as carbon dioxide) are monitored by means of chemical sensors disposed within the culture bottle.

The presence of a growing bacterial population within a culture bottle of 80 mL overall volume is typically detected when the number of microorganisms has risen to approximately $5\times10^9$ CFU (colony forming units). It is obvious that many bacterial doubling events are required to grow a bacterial population from one or two organisms in the 10 mL blood sample to such a high number. One solution to providing faster bacterial detection is splitting the 10-mL sample liquid together with the required growth media (typically 30 mL volume of growth media is combined with the 10 mL of blood) into a large number of smaller partial samples that are contained in closed small chambers. This is described in U.S. Pat. Nos. 5,770,440 and 5,891,739 to Berndt, which are incorporated by reference herein. U.S. Pat. No. 5,716,798 to Monthony et al., which is incorporated by reference herein, describes an array of small chambers (a 96 well array of 250 µl wells) that are not closed from each other, but have a joint head space volume. Monthony et al. contemplates the use of colorimetric, fluorometric, radiometric, nephelometric, and infrared analysis to assay the sample well to detect the presence or absence of bacteria therein. Monthony et al. reports that a shortening in the time to detection (TTD) is achieved with smaller sample volumes.

While the splitting of the original 10-mL blood sample together with the 30 mL of growth media is promising towards achieving faster bacterial detection, the design of a practical multi-chamber sample container for detecting the presence or absence of microorganisms in the one or more chambers is a challenge. For example, if bacterial growth is detected in only one or two of the small chambers, then these chambers need to be identified and accessed in order to remove the sample liquid from those chambers where positive growth is detected for downstream analysis such as ID (e.g. Maldi time-of-flight) and antibiotic susceptibility testing (AST). Accurately removing sample from discrete chambers in an array of small chambers represents a further challenge.

Another challenge to the implementation of an array of small-volume chambers for detecting microbial growth is the detectors that are deployed. Optical interrogation of the individual chambers requires accurate measurements to ensure that the measurement is associated with the appropriate chamber. Signal cross talk from well to well also must be avoided. The deployment of individual chemical sensors for each well can be expensive and difficult to implement.

Dielectric impedance measurement has been evaluated as an alternative to the use of chemical sensors. However, barriers to commercial deployment include the sensitivity of the impedance to temperature fluctuations. Maintaining the temperature of the blood culture bottle to better than $+/-0.05°$ C. is not practical for a clinical bacterial detection environment.

In Sengupta, S, et al., "A micro-scale multi-frequency reactance measurement technique to detect bacterial growth at low bio-particle concentrations," Lab Chip, Vol. 6, pp. 682-692 (2006), which is incorporated by reference herein, a micro-fluidic chamber of 100 µl volume was used as the chamber for sensing response to the presence of bacteria. Sengupta et al. reported that the sensing response can be improved relative to a simple dielectric conductivity measurement by providing a long and very thin channel-like chamber containing the sample, with very small electrodes positioned at both ends. By using high frequencies up to 100 MHz, the capacitive contribution of the liquid sample was measured, which, according to Sengupta et al., is more sensitive to the changes in capacitance in the sample caused by the presence and/or growth of bacteria in the chamber.

As further described in Sengupta, S., et al., "Rapid detection of bacterial proliferation in food samples using microchannel impedance measurements at multiple frequencies," Scns. & Instrumen. Food Qual., Vol. 4, pp. 108-118 (2010) and Puttaswamy, S., et al., "Novel Electrical Method for Early Detection of Viable Bacteria in Blood Cultures," J. Clin. MicroBio., Vol. 49(6), pp. 2286-2289 (2011), both of which are incorporated by reference herein, temperature fluctuations are described as the most significant challenge to the use of the Sengupta et al. apparatus and method of using a microfluidic environment to assay for the presence of bacteria in a sample using a dielectric conductivity measurement.

A further limit on the Sengupta et al. apparatus and method is the need to fill a new microfluidics chamber (or replace the liquid sample in the microfluidics chamber with fresh liquid sample from the culture bottle) after one hour or so and make the next measurement with a new sample. This approach consumes approximately 1 mL of sample liquid within ten hours, as each previously sampled portion is discarded. While sampling could happen more often to achieve a better signal-to-noise ratio; for slow growing microorganisms, the volume of sample consumption over time could represent a serious challenge.

Therefore, there exists the need for improvement if the use of dielectric measurements to detect the presence or absence of microbes in a liquid sample is to be commercially viable.

BRIEF SUMMARY OF THE INVENTION

Disclosed herein are a microbial (e.g. bacterial) detection apparatus and method that can process a macroscopic liquid sample volume of, in preferred embodiments for blood culture assays, typically 40 mL (10 mL blood; 30 mL growth media). The apparatus and method provide an assay environment that facilitates measurement of the capacitive impedance component, that does not suffer from temperature fluctuations, and that allows using a relatively simple and low-cost disposable array of chambers for the dielectric measurement of discrete sample portions that can readily be compared with dielectric measurements of other chambers in the array for baseline monitoring and improved ability to quickly assay for the presence or absence of microorganisms in the sample.

One embodiment of the present invention described herein is an impedance-based bacterial detection method. In this method a vessel containing a liquid sample suspected of containing microorganisms is provided. The vessel is configured to have electrodes positioned such that the sample is disposed between the electrodes. The liquid sample is in physical contact with at least one of the two electrodes. The vessel itself can have one or more chambers, each chamber having the electrodes positioned such that any sample in the chamber is disposed between the two electrodes. Vessels and multi-chamber plates (e.g. microtiter plates) are well known in the art and not described in detail herein.

A time-varying electrical signal is applied to the first electrode in contact with the liquid sample. The second electrode is electrically connected to a phase-sensitive signal detector. A frequency of the time-varying electrical signal is selected so that an out-of-phase signal amplitude measured by the detector becomes equal to about zero at the selected frequency. That out-of-phase signal amplitude is monitored over time with the phase-sensitive signal detector. If an increase in the signal amplitude is observed over time, this is an indication of microbial growth within the liquid sample.

In another embodiment, the impedance-based bacterial detection method provides the time-varying electrical signal to the first electrode in contact with the liquid sample. The second electrode is electrically connected to the phase-sensitive signal detector. The out-of-phase signal amplitude is monitored over time with the phase-sensitive signal detector. In this method, a frequency at which the out of phase amplitude is zero is determined by tuning a frequency of said electrical signal so that an out-of-phase signal amplitude measured by said detector becomes equal to about zero. This step is repeated at predetermined time intervals. If an increase in the frequency at which the out-of-phase signal amplitude is observes, then this is an indication of microbial growth within said liquid sample.

In another embodiment of the methods described herein the time-varying electrical signal generated by a voltage-controlled oscillator is applied to the first electrode. The second electrode is again electrically connected to a phase-sensitive signal detector. In this embodiment an integrated out-of-phase output signal of the detector is provided as a frequency-control input of the voltage-controlled oscillator whereby the oscillator is tuned to a frequency at which the out-of-phase signal amplitude measured by the detector is equal to zero. An increase in the tuned frequency over time indicates microbial growth within said liquid sample.

Other embodiments of the present invention is an apparatus for bacterial detection that impedance-based. The apparatus has a receptacle that receives the single vessel or multi-well plates described above. The single vessel or on or more chambers of the multi-well plate liquid sample suspected of containing microorganisms. Either the vessel or one of more chambers in the multi-well plate has two electrodes positioned such that the sample is disposed between and in contact with the first and second electrodes.

The apparatus has a signal source that provides a time-varying electrical signal to the first electrode that is transmitted through the liquid sample to the second electrode. The apparatus has a phase-sensitive signal detector connected to the second electrode of the vessel. The output of the signal detector indicates a change in bulk capacity of the liquid sample if it occurs.

In this embodiment, if the vessel is a multi-well plate, at least a plurality of the wells receive a liquid sample suspected of containing microorganisms. In this embodiment a de-multiplexer provides the time-varying electrical signal generated to the first electrodes of the plurality of wells in the array of wells. The apparatus also has a multiplexer for receiving the time-varying signal transmitted through the plurality of wells. The multiplexer transmits the signal to the phase-sensitive signal detector.

In another embodiment of the apparatus the phase-sensitive signal detector is a lock-in amplifier with an internal signal generator that measures an out of phase component of the signal transmitted through the liquid sample. The internal signal generator is the signal source that provides the time-varying electrical signal to the first electrode. In this embodiment the apparatus is configured to detect a change in the frequency of the internal signal generated that is required for the amplitude of the out of phase signal to reach the value zero (which change indicates microbial growth).

In another embodiment, the time-varying electrical signal is generated by a voltage-controlled oscillator to the first electrode. In this embodiment the apparatus has an integrator coupled to the output of the phase-sensitive signal detector. The output of the integrator is coupled to the input of the voltage-controlled oscillator. The oscillator is tuned to a frequency at which an out-of-phase signal amplitude measured by the detector is equal to zero. An output from the signal detector will indicates a change in tuned frequency. A change in tuned frequency is an indication of microbial growth.

In one embodiment, a 10-mL whole blood sample is mixed with 30 mL of BD BACTEC™ growth media and dispensed into an array of 96 chambers. Each chamber has a total volume of 0.42 mL. The 10 mL sample size is selected because it is an industry-accepted standard sample size for ensuring that, if microorganisms are present in a patient's bloodstream, some of those microorganisms will be present in the 10 mL sample. The skilled person will understand that the invention is not limited to sample size or culture media volume other than ensuring enough sample volume to assay the sample for the presence or absence of microorganisms as described herein.

The presence of bacteria is monitored in each chamber (or well or micro-well, which terms are used interchangeably herein) by subjecting the chamber containing sample to an RF dielectric impedance measurement. The electrode configuration will typically be a bottom electrode which serves as the bottom of the chamber and a top electrode disposed on the array and extending somewhat into the top portion of the chamber. The frequency of the measurement, the diameter of the electrodes, and the distance between the electrodes are optimized so that any change in the bulk capacitance of the sample liquid causes a change in the measured out-of-phase signal component. The out of phase signal component are signals having a different phase from the measured signal at a given frequency.

While the conductivity component is related to metabolic bacterial products such as different gases, the capacitive component is reflecting the presence of bacteria in a well. Since the presence is detected, all wells can have a joint head space, which in turn makes it possible to design a very simple and low-cost disposable with easy access to positive chambers.

Faster bacterial detection can be achieved according to the method and apparatus described herein (i) due to the use of small-volume chambers, (ii) due to comparing next neighbors in the array of chambers, and (iii) due to the fact that the capacitive detection mechanism is much more sensitive than the conductive detection mechanism.

BRIEF DESCRIPTION OF THE DRAWINGS

The following FIGS. 1 to 18 are provided to illustrate embodiments of the present invention.

FIG. 1 depicts the base of a disposable chamber array according to one embodiment of the present invention.

FIG. 2 is an illustration showing the base of the chamber array of FIG. 1 with an attached lid.

FIG. 3 illustrates a disposable base of a chamber array according to one embodiment of the present invention, filled with 40 mL of sample liquid.

FIG. 4 illustrates the filled and assembled disposable chamber array.

FIG. 5 illustrates a schematic of an impedance measurement circuit for the chambers in the array according to one embodiment of the present invention.

FIG. 6 illustrates a mechanism for interrogating the individual chambers of the disposable array.

FIG. 7 shows two plots representing the calculated out-of-phase signal component versus the circular measurement frequency for two values of the sample capacitance.

FIG. 8 shows the same two plots as in FIG. 7, but in linear Y-scaling, and only within the circular frequency range $10^5$-$10^6$ 1/s, i.e. where a zero-crossing is observed.

FIG. 9 shows the expected shortening in the time-to-detection that results from using small-volume chambers in combination with enhanced sensor resolution due to comparing next neighbors in an array, and due to measuring the capacitive impedance component.

FIG. 10 illustrates one embodiment of an apparatus for measuring the dielectric capacitance of a liquid sample to determine the presence or absence of microorganisms therein.

FIG. 11 compares the area of the 96 well plate described herein with the area of a standard 96 well test plate.

FIG. 12 illustrates the relationship between the out-of-phase signal and frequency.

FIG. 14A-C are a series of recorded spectra for different wells of identical volume and composition, as measured using a Stanford Research Systems Model SR850 100-kHz DSP lock-in amplifier in an experimental setup depicted in FIG. 10.

FIG. 15 illustrates the time/frequency relationship for media spiked with E. coli based on recorded spectra for a small well, and a growth curve recorded in parallel on a BACTEC™ blood culture instrument from Becton Dickinson Diagnostics, Sparks, Md., using a large BACTEC™ bottle, filled with the same liquid sample.

FIG. 16 illustrates the time it takes for the out-of-phase signal component to turn towards positive values due to an increasing bulk capacitance for a BACTEC™ media spiked with E. coli. The curve on the right represents a growth curve recorded in parallel on a BACTEC™ blood culture instrument from Becton Dickinson Diagnostics, Sparks, Md., using a large BACTEC™ bottle, filled with the same liquid sample.

FIG. 17 illustrates that early growth is detected if the scale of the measured out-of-phase signal is magnified.

FIG. 18 illustrates an alternate embodiment of an apparatus for measuring the dielectric capacitance of a liquid sample to determine the presence or absence of microorganisms therein whereby the measuring frequency of the signal generator is automatically tuned to and kept at the zero-crossing frequency.

DETAILED DESCRIPTION

Figure 6:
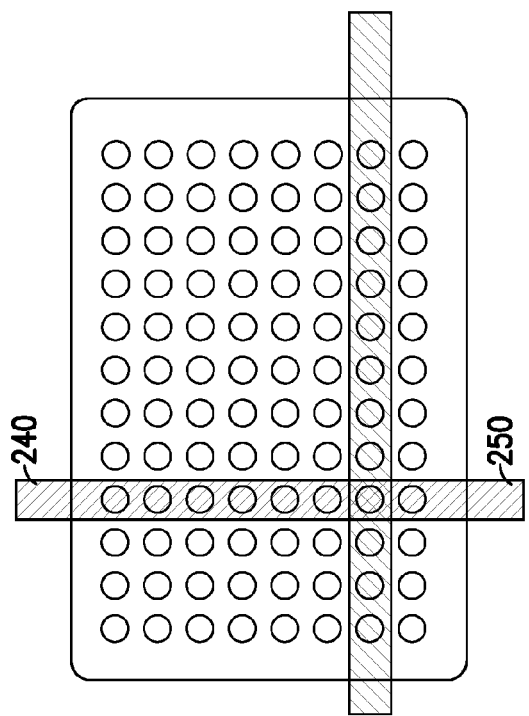

The examples of the present invention described herein are in the context of detecting for the presence or absence of bacteria in a blood sample. Unless otherwise stated, the biological sample is a 10-mL whole blood sample that is mixed with 30 mL of BD BACTEC™ growth media. The sample and media combined are dispensed into an array of 96 chambers of 0.42 mL volume each. Although numerous examples are so described, the skilled person will understand that the disclosed method and apparatus can be used to test a variety of different samples (tissue samples, sputum samples, urine samples, etc.) combined with a variety of different growth media. While the described chamber volume and chamber array are advantageous in terms of the volume of a combined blood/media sample, the skilled person can select chamber volume and array size for a particular environment.

The presence or absence of bacteria is determined using RF dielectric impedance measurement. The electrode configuration and the frequency are configured as described herein to ensure that any change in the bulk capacitance of the sample liquid causes a change in the measured out-of-phase signal component.

While the conductivity component is a measurement that is related to the presence or absence of metabolic bacterial byproducts such as different gases (e.g. $CO_2$) in the sample, the capacitive component more directly reflects the absolute presence or absence of bacteria in a well. Since the presence of the bacteria (and not the metabolic byproducts of the bacteria) is detected, all wells in the array can share a common or joint head space. This relieves the well array of a design constraint (i.e. wells or chambers isolated from each other in a gas-tight fashion), which in turn permits a very simple and low-cost disposable array of wells with easy access to those wells that contain sample determined to be positive for bacteria.

Referring to the Figures, FIG. 1 is a cut away side view of an array 100. The base 110 of the wells 120 have electrodes 130 in electrical communication with contacts 140. The volume of the wells 120 is 0.5 mL with a height of 26 mm and a diameter of 5 mm. The housing, 150, is made of plastic, making the assembly low cost.

FIG. 2 illustrates the base 110 of the wells 120 of FIG. 1 with an attached lid 170. The lid 170 has an underlying metallized layer 160 which serves as the top electrode for each well. The top electrodes extend into their respective wells such that the distance between the top electrode and the bottom electrode is 21.5 mm. In this embodiment, as described below, the 21.5 mm distance is advantageous for detecting changes in impedance attributable to the presence of bacteria in the sample.

FIG. 3 illustrates the well array of FIG. 1 with the chambers filled with sample liquid 180. Although listed in side view, the array 100 is a 96 well array (12×8) that will accept 40 mL of sample liquid among the 96 (0.5 mL) wells.

FIG. 4 illustrates the well array of FIG. 1 with the chambers filled with sample liquid 180. The effective disposable volume that is monitored for the presence of bacteria is the space between the electrodes, which is only 0.417 mL in the illustrated embodiment. The effective head space volume for the well array is 15.3 mL. Due to the joint head space, the ratio gas/liquid is higher or equal to the BACTEC™ ratio for up to 36 positive chambers. This means that for a bacterial load of up to 36 CFU per 10 mL of whole blood there would exist optimum growth conditions. For a bacterial load higher than 36 CFU per 10 mL of whole blood, the growth conditions would be somewhat less than optimum, but these cases are rare. One should keep in mind that a 10-mL blood sample is recommended to catch at least one or two microorganisms from the patients in the sample volume.

Figure 5:
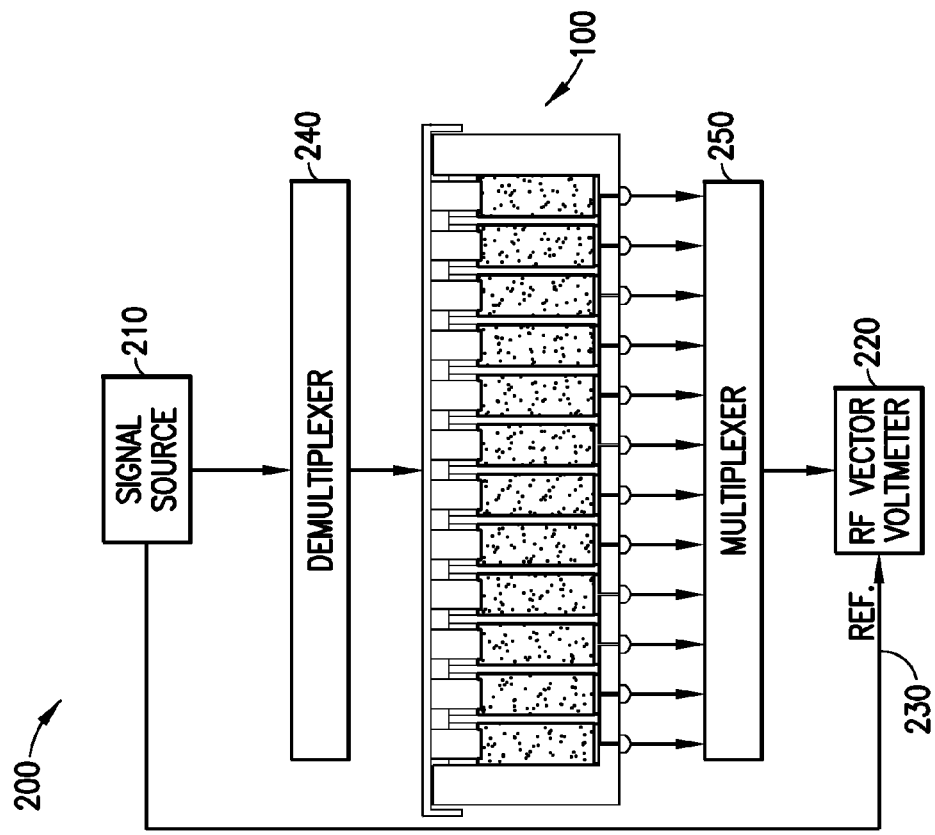

FIG. 5 illustrates a schematic of an impedance measurement circuit 200 for the wells 120 in the array 100 according to one embodiment of the present invention. In this embodiment, a signal source 210 is applied to a top electrode 120 and a vector voltmeter 220 is used to detect the impedance of the sample 180 and changes in impedance relative to a reference voltage 230. Demultiplexers 240 and multiplexers 250 are deployed to ensure that the signal is applied and read well by well.

FIG. 6 illustrates a mechanism for interrogating the individual chambers of the disposable array. All 96 chambers can be individually interrogated using an 8-channel demultiplexer 240 to address the upper electrodes, and a 12-channel multiplexer 250 for signal pick-up at the lower electrodes.

Figure 7:
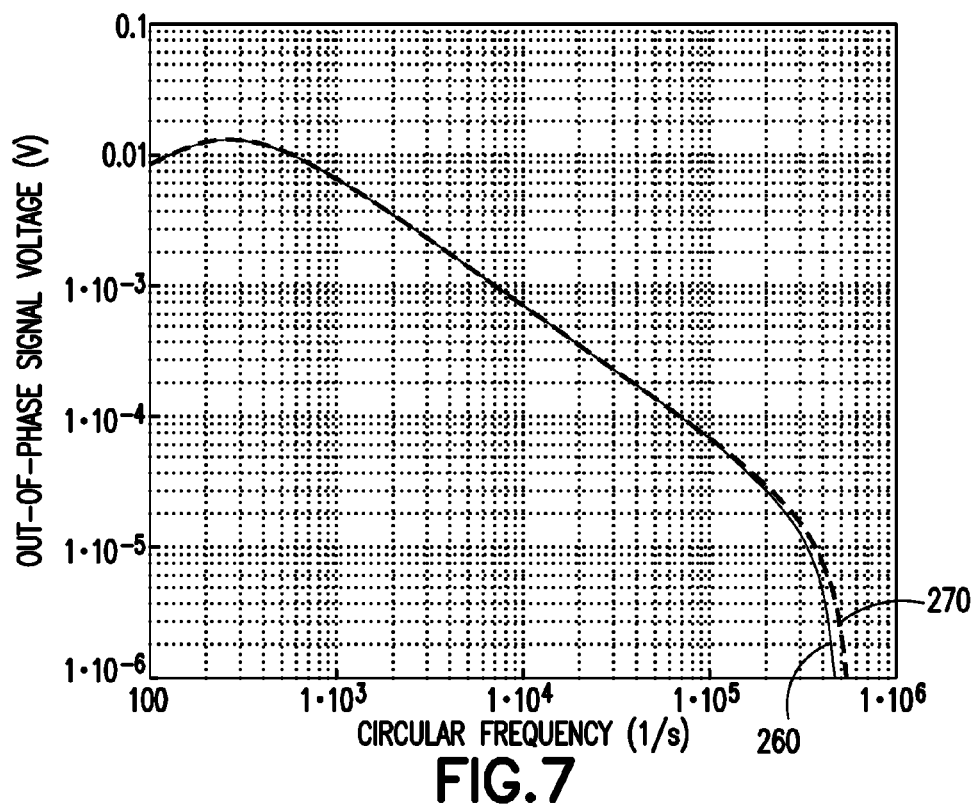

FIG. 7 illustrates two plots representing the calculated out-of-phase signal component versus the circular measurement frequency ($\omega=2\Pi f$) for two values of the sample capacitance. These measurements are for a single well. The solid line 260 is for a well with a capacity of 0.66 pF due to its bacterial load. The dashed line 270 is for a well with a capacity twice that of the well from which the solid line signal was measured. Note that, at lower frequencies, there is no difference in the out-of-phase signal of the two wells, despite the different bacteria-induced capacities. However, at higher frequencies, different signals for different bacteria concentrations were observed.

Figure 8:
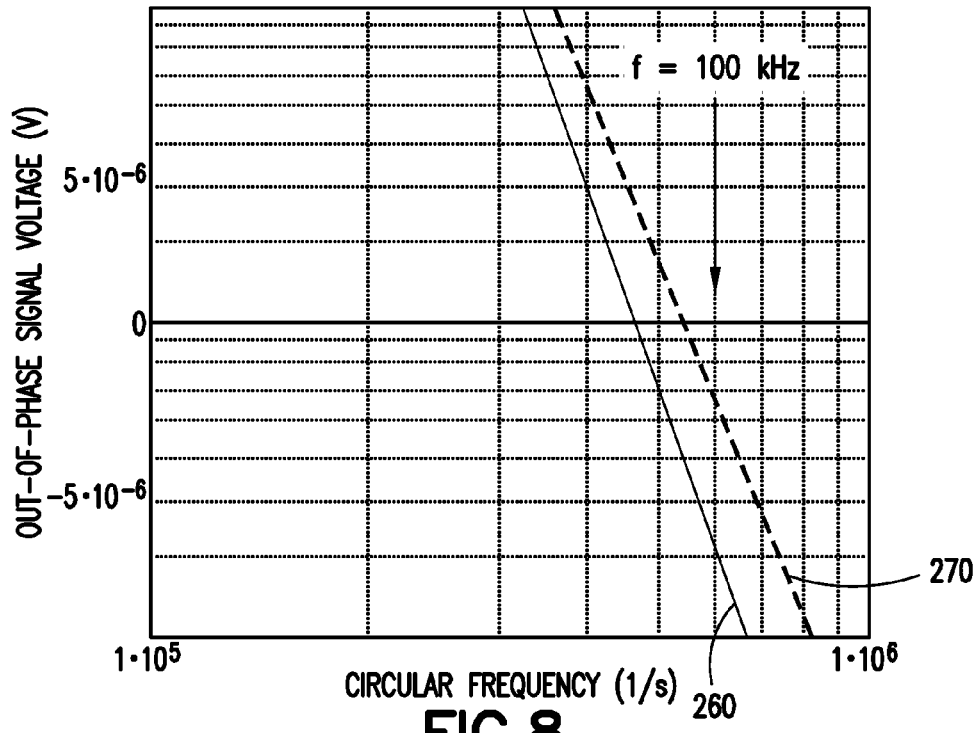

FIG. 8 shows the same two plots as in FIG. 7, but in linear Y-scaling, and only within the circular frequency range $10^5$-$10^6$ 1/s, where a bulk-capacity dependent zero-crossing frequency is observed. Since an increasing number of bacteria within the bulk suspension are expected to increase the bulk capacitance, bacterial growth is expected to cause a shift in the initial zero-crossing frequency to higher values. It is also possible according to the embodiments described herein to determine the initial zero-crossing frequency, to tune the measuring frequency to this value, and to monitor the out-of-phase signal amplitude over time. An increase in the number of bacteria in the suspension would then cause an increase in the out-of-phase signal amplitude. In other words, the presence of a growing population of bacteria can be detected by monitoring the out-of-phase signal amplitude over time.

Figure 9:
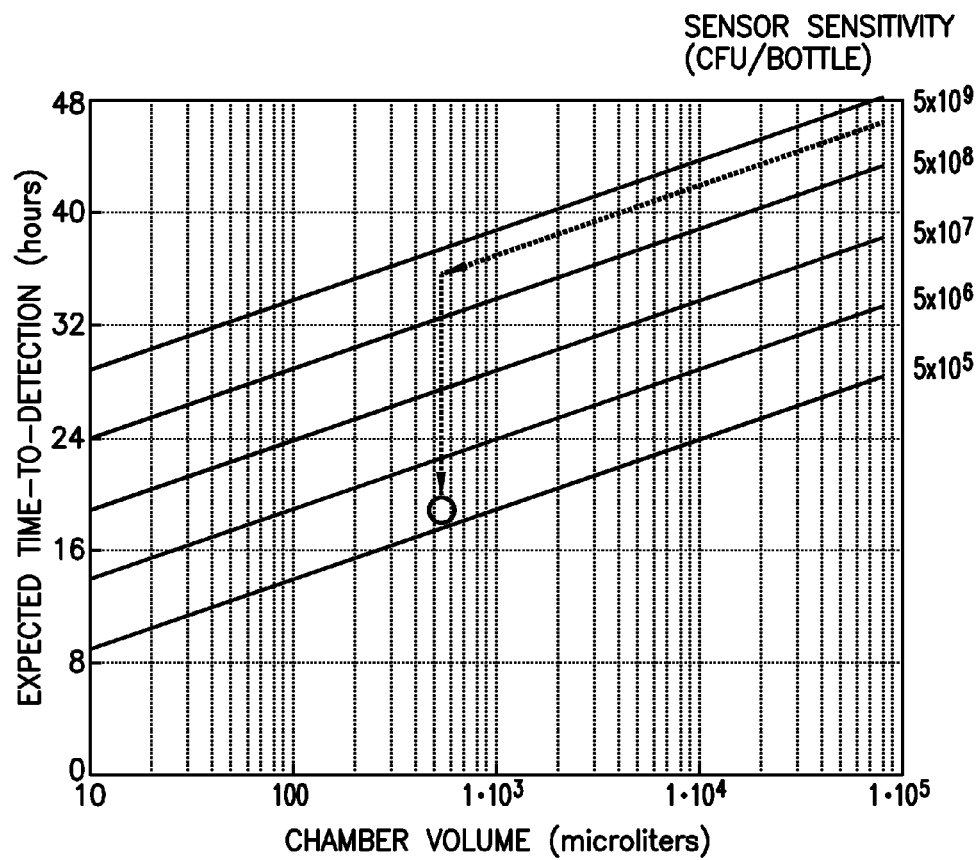

FIG. 9 illustrates the expected shortening in the time-to-detection that results from using small-volume wells in combination with enhanced sensor resolution due to comparing next neighbors in an array, and due to measuring the capacitive impedance component. Specifically, FIG. 9 illustrates that, for sensors of all sensitivity, a decrease in volume provides for a decrease in time to detection. Lowering the volume from that of the standard BACTEC™ bottle ($8\times10^4$ μl) to the volume of the wells described in the embodiments herein (500 μl) provide for a significantly reduced time to detection.

Faster bacterial detection is achieved by the apparatus and method described herein (i) due to the use of small-volume chambers (e.g. 0.5 mL or less), (ii) due to the ability to compare the measurement of one well with the measurement obtained from a neighboring well in real time, and (iii) due to the fact that the frequency-dependent capacitive detection mechanism is much more sensitive than the conductive detection mechanism.

As noted above, the method and apparatus of the present invention can be used with a wide array of samples and growth media. The testing environment can be tailored to the sampling environment to provide a favorable number of wells for the sample volume (combined with media). It is advantageous if the media is only weakly conductive as this makes change in impedance due to the presence of bacteria, measured as change in bulk capacitance, easier to measure. The macroscopic well arrays are easier to work with than the micro-fluidic chambers deployed in prior art to measure a change in capacitance of the sample, need only one filling, are disposable, and can accept and monitor a full 10-mL blood sample. Also, bacteria will grow in the macroscopic wells described herein and will experience slow growth or no growth in an enclosed microfluidic environment without sufficient head space volume.

Furthermore, an open array of micro-wells will provide a sufficient amount of oxygen for optimum growth of aerobic microorganism species during the whole growth process due to the joint head space. There is no need for sealed chambers, because no gaseous metabolites are monitored. Enhanced practical sensing resolution is achieved due to the use of an array of wells that enables real time well to well comparison of the impedance measurements. The present invention is advantageous because it does not require the use of a chemical sensor. The open array is not only inexpensive and disposable, it is also suitable for use with robotic automation such as dispensing and extracting of blood sample and transfer of sample from positive chambers into other wells or a second disposable of similar design for downstream ID/AST procedures on same instrument.

Figure 10:
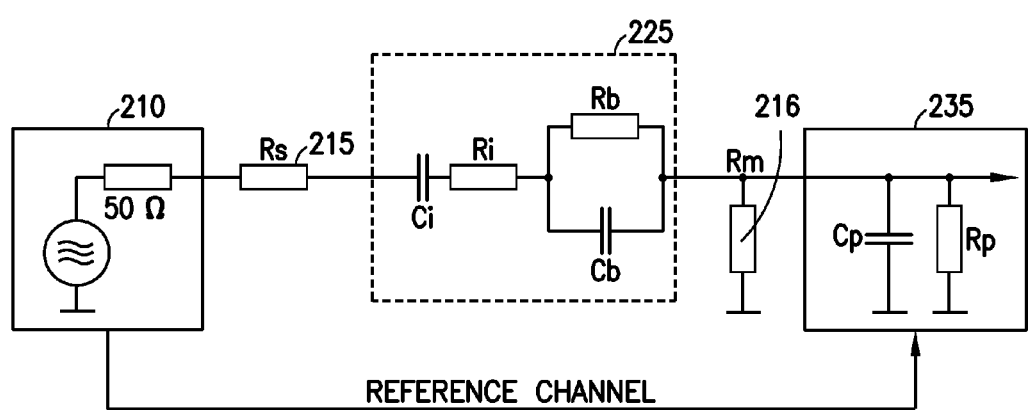

FIG. 10 is a more detailed illustration showing an apparatus according to one embodiment of the present invention. A common lock-in amplifier containing an internal signal generator 210 is used to feed a sinusoidal RF signal to one electrode of a dielectric impedance measuring chamber 220. The second electrode of said chamber is connected with the signal input 235 of said lock-in amplifier.

As is known to someone skilled in the art, the sample liquid within said chamber, which is in direct contact with the two electrodes, can be described by the electrical network shown in the dashed box 225 of FIG. 10. Hereby, Ci represents the interface capacitance between the metal electrodes and the liquid, Ri represents the interface resistance between the metal electrodes and the liquid, Rb is the bulk resistance of the liquid, and Cb is the bulk capacitance.

It is assumed that the lock-in amplifier internal signal generator 210 has a typical internal resistance of 50Ω, and that the lock-in amplifier input stage 235 has a typical capacitance of 15 pF and a typical input resistance of 10 MΩ.

According to the present invention, a source-matching resistor Rs (215), as shown in FIG. 10, and a measuring load resistor Rm (216), also shown in FIG. 10, can be selected so that, for a given dielectric measuring chamber and liquid, the frequency spectrum of the out-of-phase component of the measurement signal shows a zero-crossing feature that (i) is dependent on the value of Cb, and (ii) is positioned at a conveniently low frequency below 100 kHz, allowing the use of standard lock-in amplifiers. The data recorded in the accompanying figures has been obtained with a Stanford Research Systems Model SR850 100-kHz DSP lock-in amplifier. It has been found that Rs=500Ω and Rm=500Ω are producing zero-crossing frequencies within the range 30-100 kHz for typical blood culture growth media such as Standard Aerobic/F from Becton Dickinson Diagnostics in Sparks, Md. In an apparatus according to FIG. 10, the out-of-phase signal amplitude as measured with the lock-in amplifier 235 is inversely proportional to the out-of-phase impedance value. In other words, the out-of phase impedance value is at its maximum at a zero-crossing frequency of the out-of-phase signal amplitude as measured in the manner described herein. It should be understood that the apparatus illustrated in FIG. 10 is only one example. The skilled person will understand that the method and apparatus described herein can be reduced to practice by using any appropriate signal generator and any appropriate vector voltmeter as indicated in the apparatus illustrated in FIG. 5.

It should be noted that changing the dimensions of the impedance measuring chamber, or replacing the growth media with another liquid sample, will result in other optimum values for Rs and Rm.

Figure 11:
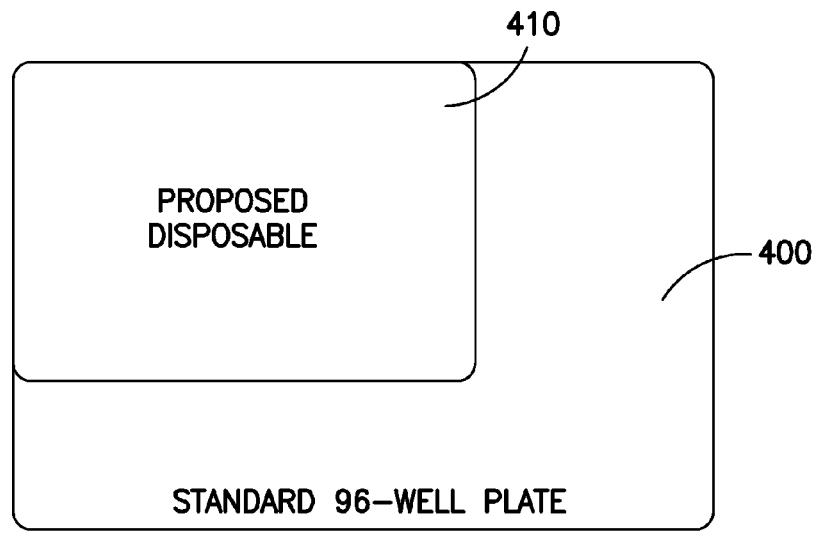

FIG. 11 compares the area of the 96 well plate 410 described herein with the area of a standard 96 well test plate 400. The test well plate described herein has a substantially reduced area compared to the standard 96 well test plate.

Figure 12:
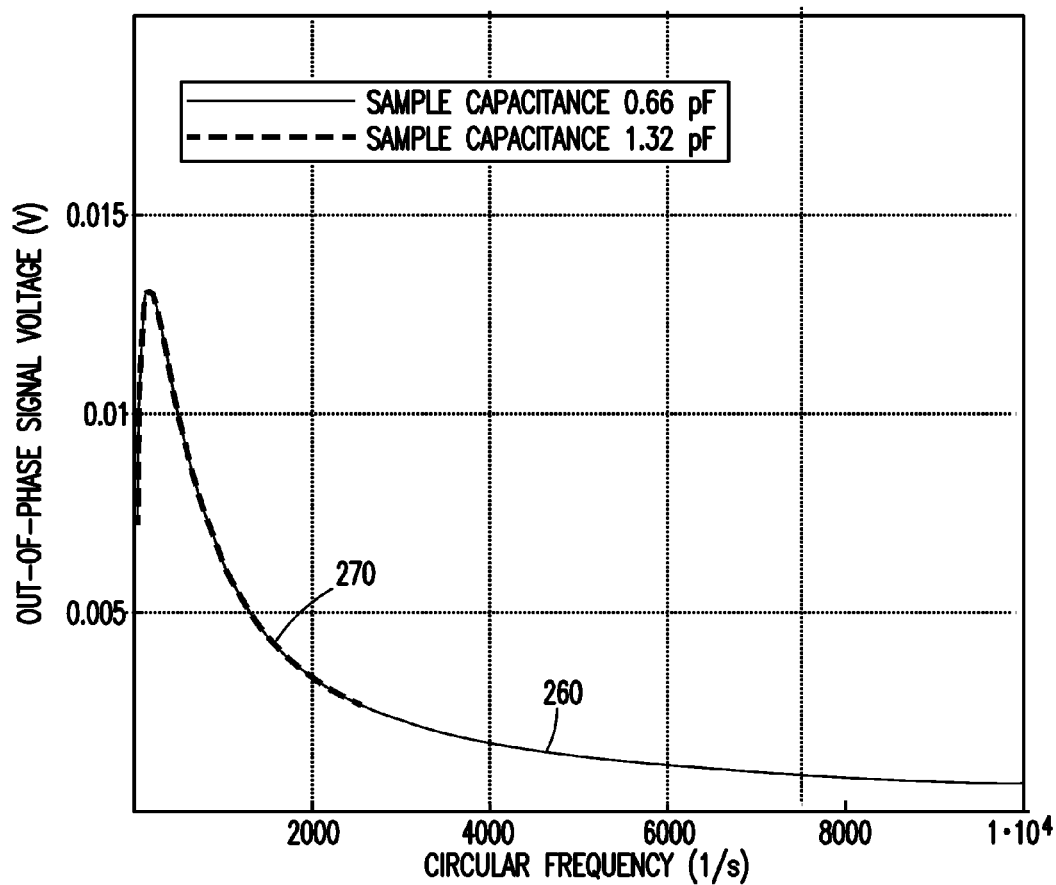

As discussed above in the context of FIG. 10, the method described herein leverages the relationship between bulk capacitance and the frequency spectrum of the out-of phase-component of the measurement signal. For better comparison between calculated and actually measured frequency spectra, FIG. 12 shows the calculated spectrum from FIG. 7, but in linear scaling. Again, at lower circular frequencies the spectrums for samples having the two different capacitance are virtually identical.

Figure 13B:
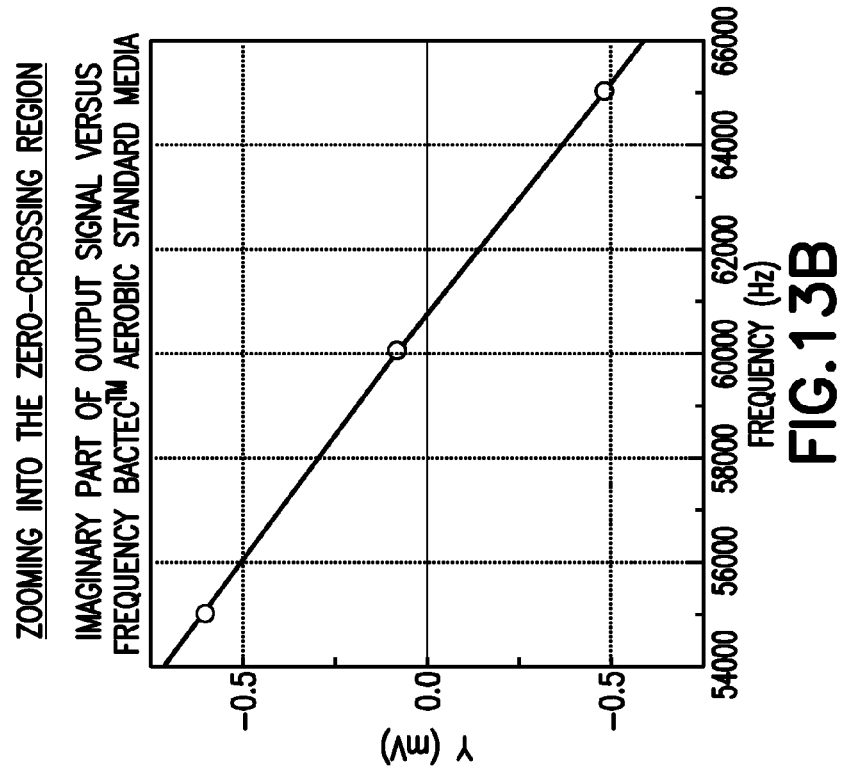
FIGS. 13A and 13B represent actual data further illustrating the relationship between frequency and the out-of-phase signal (referred to as the imaginary portion of the signal).
Figure 13A:
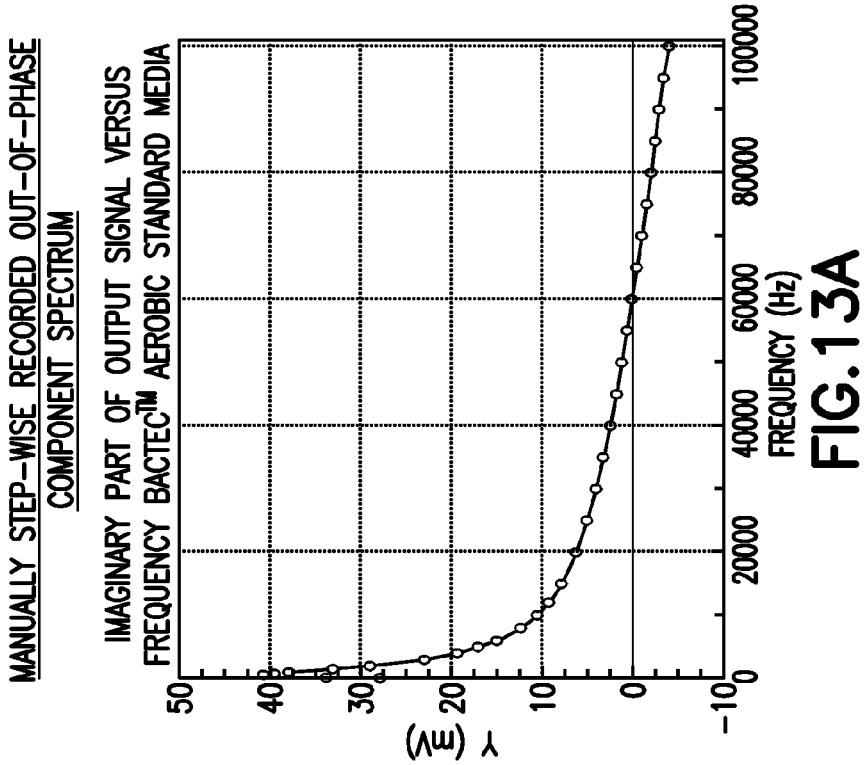
Figures 14, 14A, 14B, 14C:
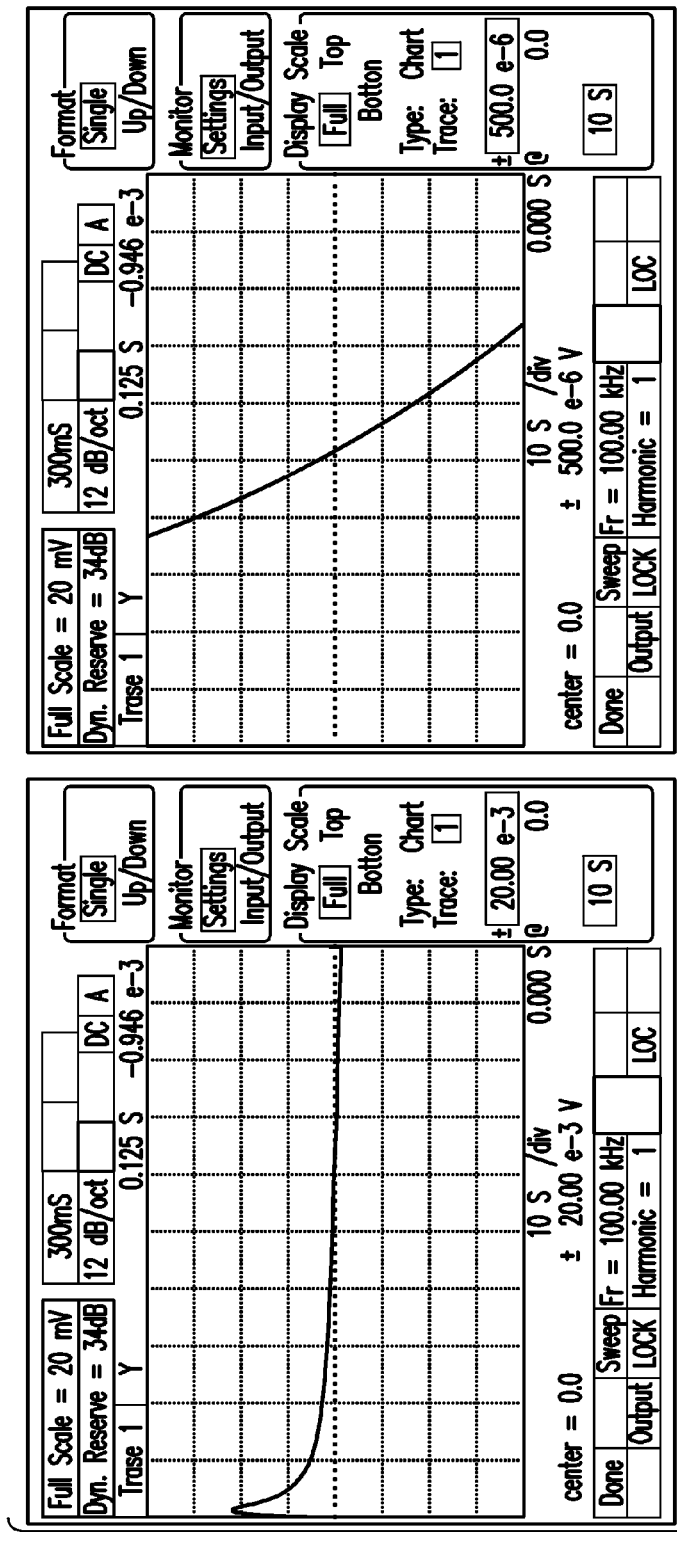
Figure 14B:
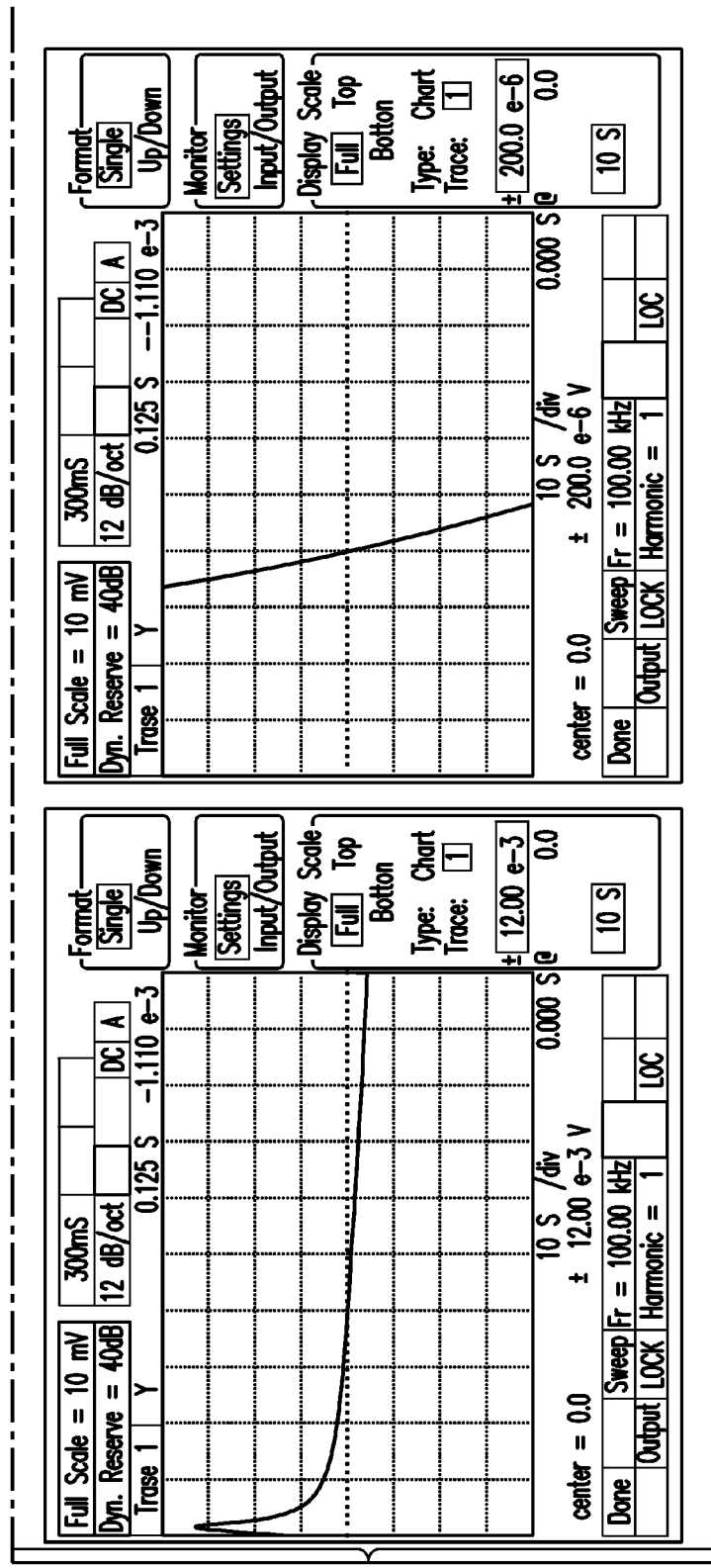
Figure 14C:
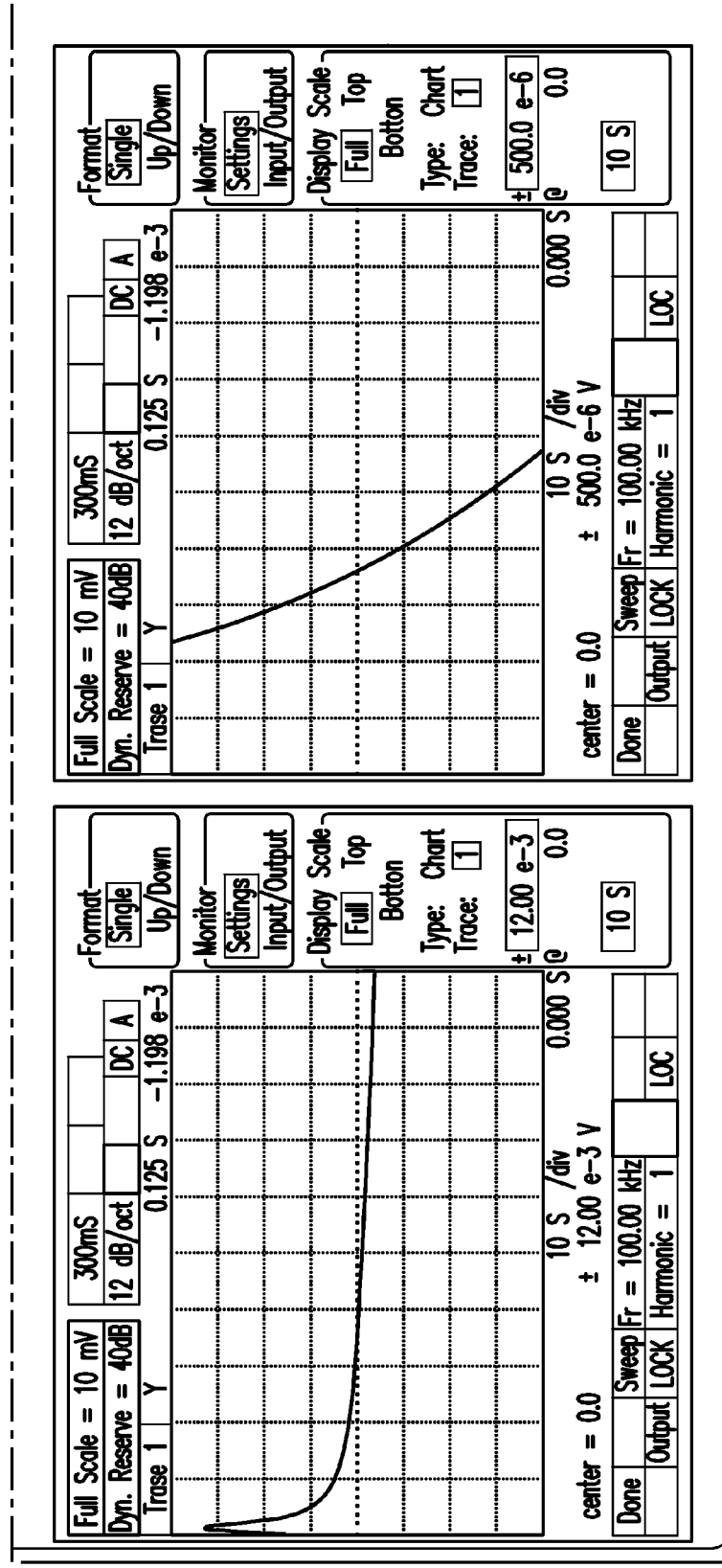

The plots in FIGS. 13A and 13B show actually recorded data using Becton Dickinson BACTEC™ Standard Aerobic/F growth media, without bacteria. As can be seen from FIG. 13A, the recorded spectrum looks very similar to the calculated one shown in FIG. 12. In this case, a zero-crossing feature is observed near 60 kHz. The plot shown in FIG. 13B is best understood when compared with FIG. 8. Due to the fact that no bacteria are present in the actual sample, only one zero-crossing frequency is observed in FIG. 13B. The screen images shown in FIGS. 14A to 14C indicate that very similar frequency spectra with a zero-crossing feature are observed for all wells that are interrogated. Note that each well shows a different zero-crossing frequency, even if each well is filled with the same amount of growth media. However, this does not present a problem since an automated instrument will determine the zero-crossing frequency for each well, and the determination of possible bacterial growth is performed at these frequencies.

As previously noted, the concentration of bacteria growing in a sample affects the bulk capacitance of the sample (all other factors being the same).

Figure 15:
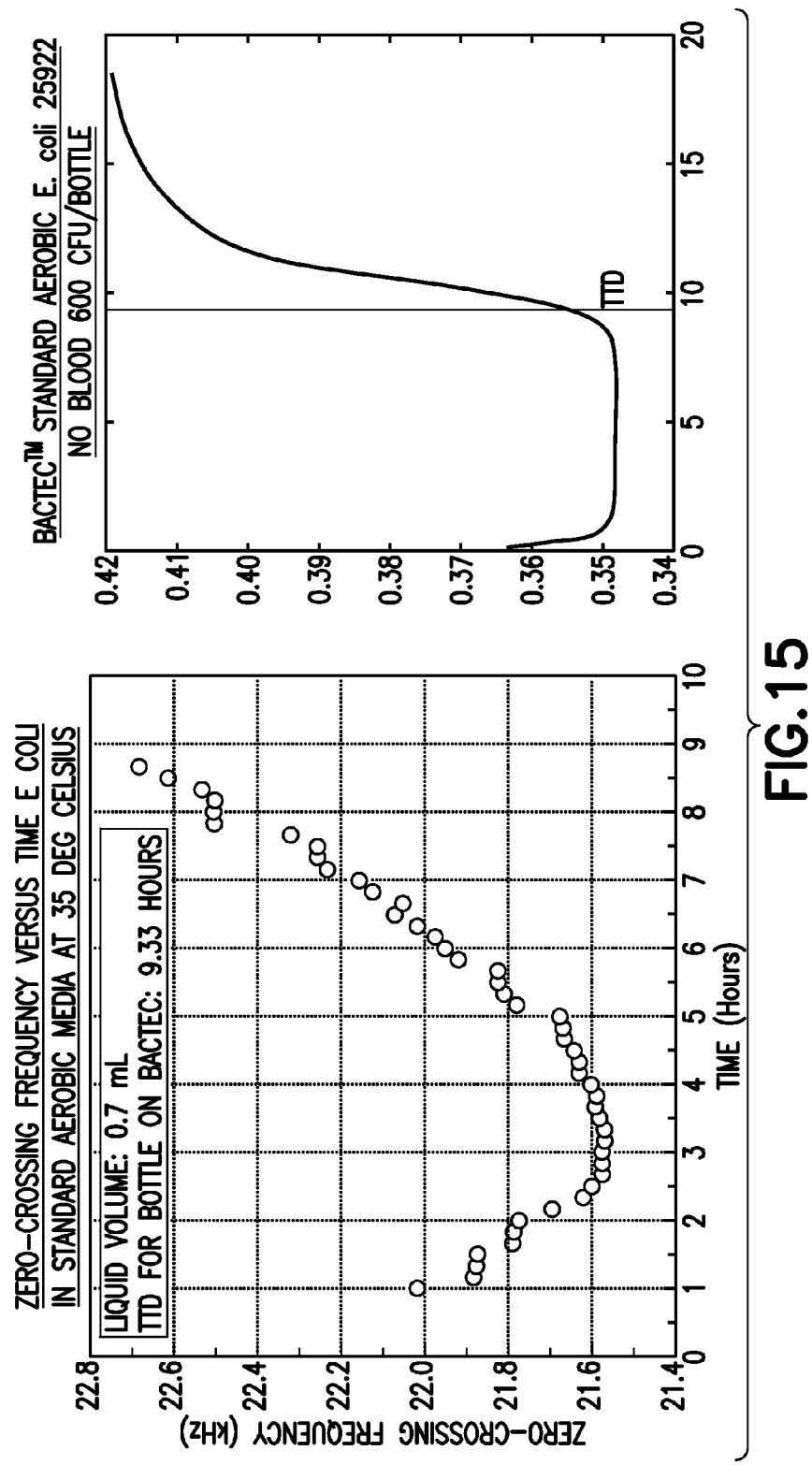

FIG. 15 illustrates that, for a given sample, a change in bacterial concentration will result in a change in frequency at which the out-of-phase signal is zero. Therefore, one skilled in the art will appreciate that one can detect bacterial growth by monitoring the frequency of this zero-crossing feature of the out-of-phase signal. A change in the frequency towards higher frequencies is a change in bacteria concentration attributable to bacterial growth. The plot on the left in FIG. 15 shows such change towards higher frequencies at about 3.5 hours after incubation. In other words, the presence of a growing bacterial population was detected after 3.5 hours. The plot on the right in FIG. 15 is the growth curve measured on a BACTEC™ instrument for a BACTEC™ bottle containing the very same sample liquid. In this case, the presence of bacteria was detected at 9.33 hours.

Instead of determining a possible shift in the zero-crossing frequency every 10 minutes as in FIG. 15, one could determine an initial zero-crossing frequency only once, operate the setup at this fixed frequency, and monitor the time course of the out-of-phase signal amplitude. If there were no drift effects, and no bacterial growth would happen, said amplitude would stay at Zero. Bacterial growth would cause a change in signal amplitude towards positive values as a consequence of an increasing bulk capacitance.

Figure 16:
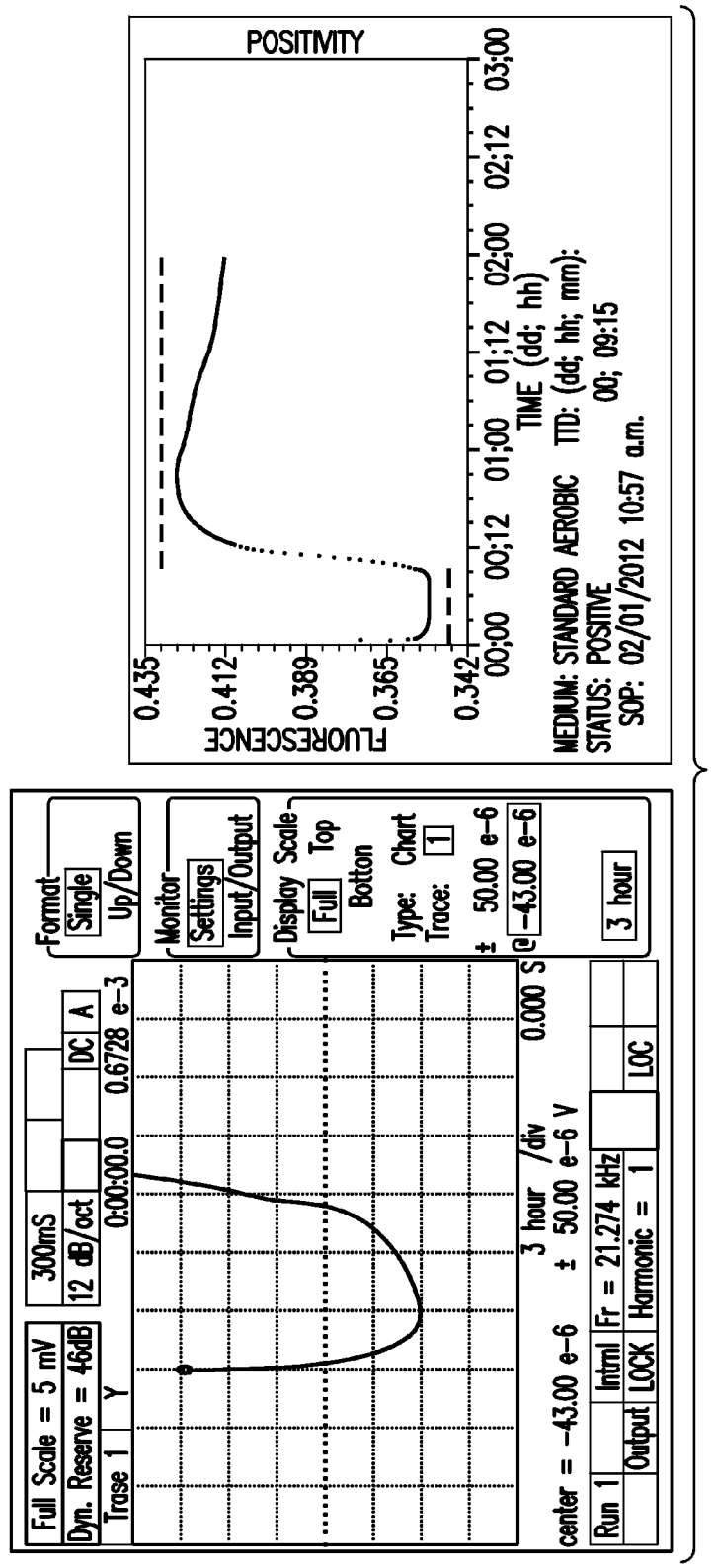

In practical experimental setups, there may be a drift in the signal amplitude over time. A drift towards negative amplitude values for the BACTEC™ Standard Aerobic/F growth media is observed. This is shown in FIG. 16, where the frequency was fixed at the initial zero-crossing value, and then the out-of-phase signal amplitude was recorded over time. As can be seen, the signal amplitude is moving towards negative values after incubation, but turns sharply towards positive values after three hours. This means the presence of a growing bacterial population was detected after three hours. A BACTEC™ growth curve, shown on the right in FIG. 16 for comparison, reveals the presence of bacterial growth after 9.25 hours.

Figure 17:
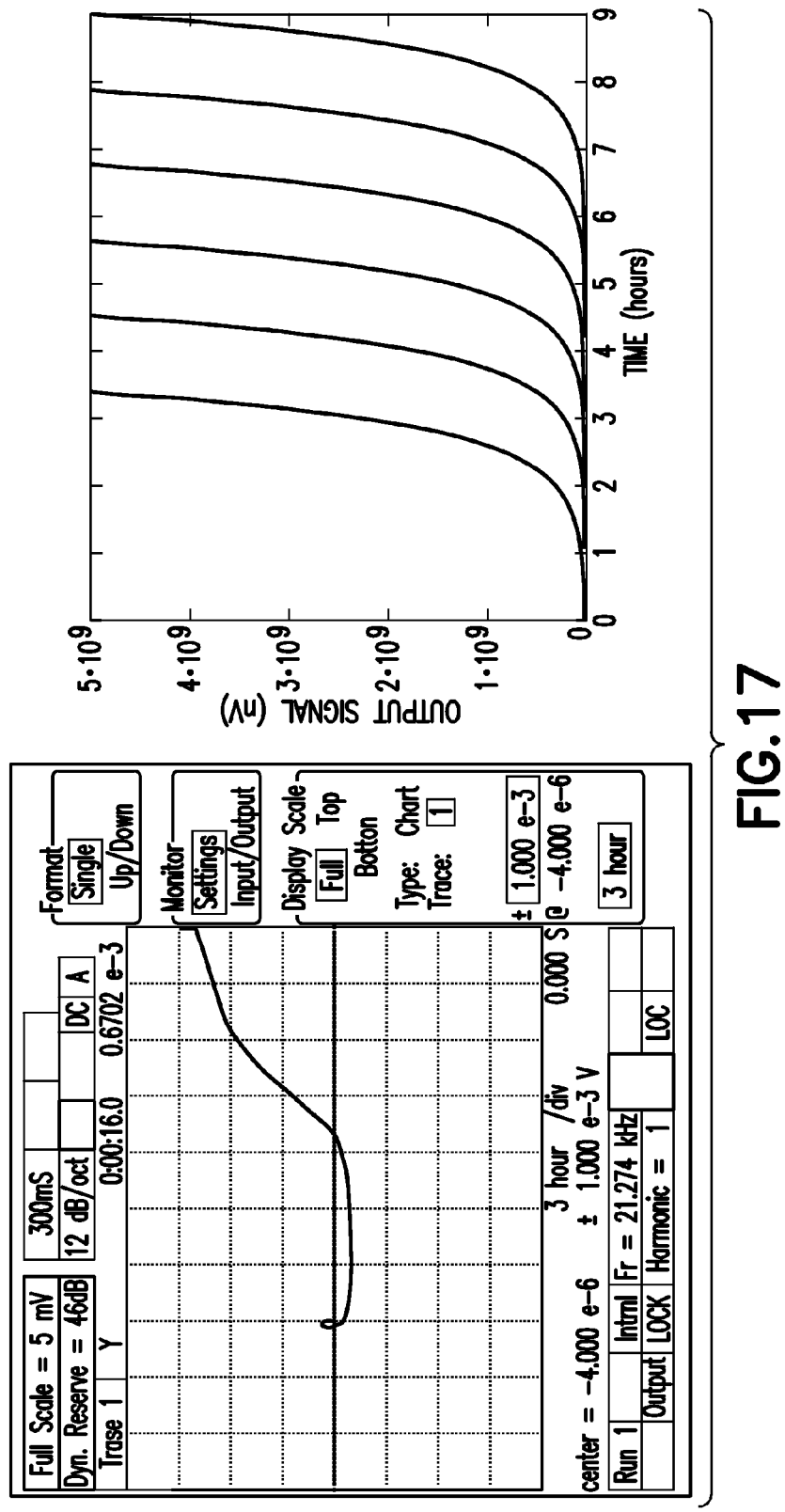

The "growth curve" on the left in FIG. 16 shows a very steep increase. FIG. 17 illustrates the complete data set of the curve shown in FIG. 16. This curve shows a further steep increase after approximately 9 hours, i.e. when the culture bottle on the BACTEC™ instrument became positive. Although applicant does not wish to be held to a particular theory, applicant submits this is indicative of the chemical sensor response to more robust chemical changes in a culture bottle. The bulk-capacitance related impedance approach is much more sensitive. The growth curves on the right in FIG. 17 illustrate that, even with different degrees of "y-zooming" to the exclusion of zooming in x, only one curve shows growth within two hours. Consequently, bacterial growth may very well take place long before a typical chemical sensor can detect it.

Figure 18:
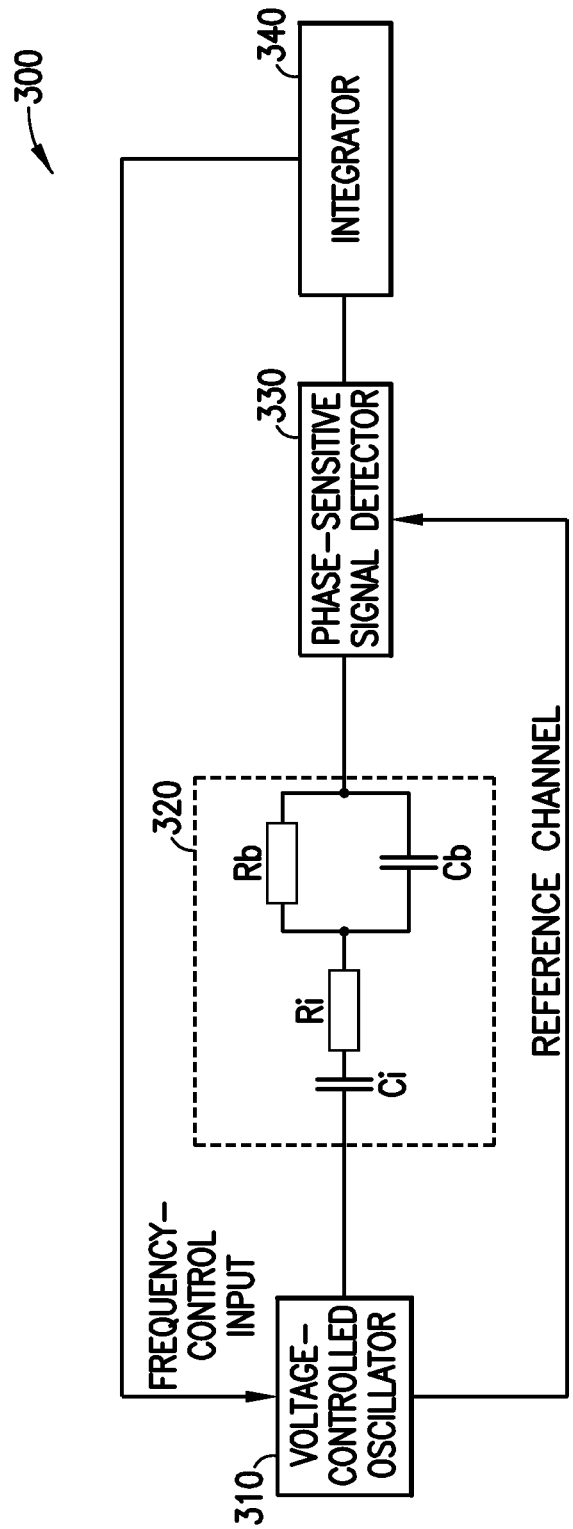

FIG. 18 illustrates an alternate embodiment of an apparatus for measuring the dielectric capacitance of a liquid sample to determine the presence or absence of microorganisms therein that was described in FIG. 10 but with automatic tuning of the measurement frequency to the bacteria-dependent zero-crossing frequency. The out-of-phase signal output of a phase-sensitive signal detector is connected to the input of an electronic integrator. The output of the integrator is connected to the frequency-control input of a voltage-controlled oscillator that acts as the signal generator as in the apparatus shown in 210A FIG. 10. Again, Ci represents the interface capacitance between the metal electrodes and the liquid, Ri represents the interface resistance between the metal electrodes and the liquid, Rb is the bulk resistance of the liquid, and Cb is the bulk capacitance.

In this embodiment, a sinusoidal electrical signal is generated by a voltage-controlled oscillator ("VOC") and electrically coupled to an electrode 460 in contact with the sample. A second electrode, also in contact with the sample, is electrically connected to a phase-sensitive signal detector. The out-of-phase output signal of the phase-sensitive signal detector is coupled to an integrator. The output of the integrator is coupled to the frequency-control input of the VOC. This causes the frequency of the VOC to be tuned until the out-of-phase signal amplitude measured by the phase-sensitive signal detector is zero. Over time, an increase in the tuned frequency indicates microorganism growth within the sample.

In operation, the integrator output voltage is affecting the frequency of the voltage-controlled oscillator. This can be explained e.g. by referring to FIGS. 13A and 13B. If in this example the starting frequency is below 60 kHz, the out-of-phase signal amplitude is positive. This leads to a positive output voltage at the integrator output and, consequently in an increase in the frequency of the voltage-controlled oscillator. The increase in frequency will continue until the zero-crossing frequency is reached. At this moment, the out-of-phase amplitude becomes zero, and no further integration occurs, leaving the frequency of the voltage-controlled oscillator at the zero-crossing frequency, which is 60.723 kHz in this example. If the initial frequency is too high, the actual zero-crossing frequency would be automatically approached from the too high frequency. The presence of bacteria could be detected by recording the zero-crossing frequency over time, and looking for an increase.

The advantage of the apparatus according to FIG. 18 is that a zero-crossing frequency can be determined with extremely high precision. Due to the fact that a "Zero Signal" is generated at the output of the phase-sensitive signal detector, any drift in the signal generator amplitude or in the internal gain of the phase-sensitive signal detector will have no effect on the automatically tuned zero-crossing frequency, which represents the system output information.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An impedance-based microbial growth detection method comprising the steps of:
   providing at least one vessel containing a liquid sample suspected of containing microorganisms disposed between and in contact with a first electrode and a second electrode;
   providing a time-varying electrical signal to the first electrode in contact with the liquid sample, wherein the second electrode is electrically connected to a phase-sensitive signal detector; and
   selecting a frequency of said time-varying electrical signal so that an out-of-phase signal amplitude measured by said phase-sensitive signal detector becomes equal to zero at the selected frequency;
   measuring the out-of-phase signal amplitude over time with the phase-sensitive signal detector at the selected frequency, wherein an increase in the signal amplitude over time at the selected frequency indicates microbial growth within the liquid sample; and
   after measuring, detecting the presence or absence of microbial growth.

2. The method of claim 1 wherein the at least one vessel is an array of vessels at least a plurality of which contain the liquid sample suspected of containing microorganisms disposed between and in contact with the first electrode and the second electrode disposed on the array of vessels, the method further comprising:
   providing a time-varying electrical signal generated to the first electrode of the plurality of vessels in the array of vessels, and
   receiving the time-varying signal transmitted through the plurality of vessels; and
   transmitting the signal to the phase-sensitive signal detector.

3. The method of claim 2 wherein the array of vessels share a common head space.

4. The method of claim 1 wherein the volume of the sample is about 40 mL.

5. The method of claim 1 wherein the sample is combined with growth media in which microorganisms, if present in the sample, will grow.

6. The method of claim 5 wherein the sample is about 10 mL of blood combined with about 30 mL of growth media.

7. The method of claim 1 wherein the first electrode is a bottom electrode that forms the bottom of the vessel and the second electrode is a top electrode extending into the vessel to contact the sample.

8. An impedance-based microbial growth detection method comprising the steps of:
   providing a sample container having at least one vessel containing a liquid sample suspected of containing microorganisms disposed between and in contact with a first electrode and a second electrode;
   providing a time-varying electrical signal to the first electrode in contact with the liquid sample, wherein the second electrode is electrically connected to a phase-sensitive signal detector; and
   measuring an out-of-phase signal amplitude over time with the phase-sensitive signal detector,
   determining a frequency at which the out of phase amplitude is zero by tuning the frequency of said electrical signal so that the out-of-phase signal amplitude measured by said detector becomes equal to zero;
   repeating the determining step at predetermined time intervals; and
   after measuring and repeated determining, detecting the presence or absence of microbial growth,
   wherein an increase in said frequency over time is an indication of microbial growth within said liquid sample.

9. The method of claim 8 wherein the at least one vessel is an array of vessels at least a plurality of which contain the liquid sample suspected of containing microorganisms disposed between and in contact with the first electrode and the second electrode disposed on the array of vessels, and the impedance-based detection method further comprising:
   providing a time-varying electrical signal generated to the first electrode of the plurality of vessels in the array of vessels, and receiving the time-varying signal transmitted through the plurality of vessels; and transmitting the time-varying signal to the phase-sensitive signal detector.

10. The method of claim 9 wherein the array of vessels share a common head space.

11. The method of claim 9 wherein the first electrode is a bottom electrode that forms the bottom of the vessels and the second electrode is a top electrode extending into the array of vessels to contact the sample.

12. The method of claim 8 wherein the volume of the sample is about 40 mL.

13. The method of claim 8 wherein the sample is combined with growth media in which microorganisms, if present in the sample, will grow.

14. The method of claim 13 wherein the sample is about 10 mL of blood combined with about 30 mL of growth media.

\* \* \* \* \*